US007984713B2

(12) United States Patent
Hochrainer et al.

(10) Patent No.: US 7,984,713 B2
(45) Date of Patent: Jul. 26, 2011

(54) POWDER INHALER HAVING A NOZZLE WITH A PLURALITY OF CHANNELS

(75) Inventors: Dieter Hochrainer, Schmallenberg (DE); Stephen Terence Dunne, Stowmarket (GB); Georg Boeck, Laupheim (DE); Joerg Schiewe, Mainz (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 1436 days.

(21) Appl. No.: 11/072,374

(22) Filed: Mar. 4, 2005

(65) Prior Publication Data
US 2005/0263151 A1    Dec. 1, 2005

(30) Foreign Application Priority Data
Mar. 5, 2004    (DE) .................. 10 2004 012 093

(51) Int. Cl.
*A61M 15/00*    (2006.01)
*A61M 16/00*    (2006.01)
(52) U.S. Cl. ......... 128/203.19; 128/200.23; 128/203.15; 128/203.21; 128/200.14; 128/205.21
(58) Field of Classification Search ............. 128/200.23, 128/203.15, 203.19, 203.21, 200.14, 205.21
See application file for complete search history.

(56) References Cited

U.S. PATENT DOCUMENTS

| 3,921,637 | A | * | 11/1975 | Bennie et al. | 128/203.15 |
| 5,161,524 | A | * | 11/1992 | Evans | 128/203.15 |
| 5,497,944 | A | * | 3/1996 | Weston et al. | 239/321 |
| 5,507,281 | A | * | 4/1996 | Kuhnel et al. | 128/203.15 |
| 5,645,050 | A | * | 7/1997 | Zierenberg et al. | 128/203.15 |
| 5,683,361 | A | | 11/1997 | Elk et al. | |
| 6,089,228 | A | * | 7/2000 | Smith et al. | 128/203.15 |
| 6,257,233 | B1 | | 7/2001 | Burr et al. | |
| 6,408,846 | B1 | | 6/2002 | Ohki et al. | |
| 6,503,362 | B1 | * | 1/2003 | Bartels et al. | 156/345.17 |
| 6,546,929 | B2 | | 4/2003 | Burr et al. | |

(Continued)

FOREIGN PATENT DOCUMENTS
EP    1062962 A    12/2000
(Continued)

OTHER PUBLICATIONS

International Search Report for corresponding application PCT/EP2005/002131, dated Jul. 22, 2005.
(Continued)

*Primary Examiner* — Steven O Douglas
*Assistant Examiner* — Clinton Ostrup
(74) *Attorney, Agent, or Firm* — Michael P. Morris; David L. Kershner

(57) ABSTRACT

The invention relates to a powder inhaler (1) with mouthpiece (2) for dispersing pharmaceutical medicament formulations, which comprises an auxiliary energy source in the form of a pressure medium system (3), having a device for supplying (6) a powder formulation (7), while on activation of the pressure medium system a gaseous pressure medium (8) released by the pressure medium system (3) forms an aerosol (9) with the powder formulation (7) such that the powder particles are present in the gaseous pressure medium (8) in dispersed form. This is achieved by means of a powder inhaler (1) comprising a multi-channel nozzle, the channels of which are inclined to one another at an angle such that the aerosol jets flowing through them meet one another downstream behind the nozzle (10).

23 Claims, 3 Drawing Sheets

U.S. PATENT DOCUMENTS

| | | | |
|---|---|---|---|
| 7,153,567 B1 * | 12/2006 | Akedo et al. | 428/323 |
| 7,246,617 B1 * | 7/2007 | Harmer et al. | 128/203.15 |
| 7,708,011 B2 | 5/2010 | Hochrainer et al. | |
| 7,736,731 B2 | 6/2010 | Akedo et al. | |
| 7,870,856 B2 | 1/2011 | Boeck | |
| 2001/0029948 A1 * | 10/2001 | Ingle et al. | 128/203.15 |
| 2002/0017297 A1 | 2/2002 | Burr et al. | |
| 2002/0033177 A1 | 3/2002 | Ohki et al. | |
| 2002/0092520 A1 * | 7/2002 | Casper et al. | 128/200.22 |
| 2003/0015194 A1 * | 1/2003 | Schiewe et al. | 128/203.15 |
| 2003/0079744 A1 | 5/2003 | Bonney et al. | |
| 2004/0187867 A1 * | 9/2004 | Hughes et al. | 128/203.15 |
| 2004/0187868 A1 * | 9/2004 | Hochrainer et al. | 128/203.15 |
| 2005/0247312 A1 * | 11/2005 | Davies | 128/203.15 |
| 2005/0263151 A1 | 12/2005 | Hochrainer et al. | |
| 2007/0240713 A1 | 10/2007 | Boeck | |
| 2008/0230058 A1 | 9/2008 | Burr et al. | |
| 2009/0194105 A1 | 8/2009 | Besseler et al. | |
| 2009/0235929 A1 | 9/2009 | Egen et al. | |
| 2010/0024815 A1 | 2/2010 | Kladders | |

FOREIGN PATENT DOCUMENTS

| | | | |
|---|---|---|---|
| WO | 9962495 A2 | | 12/1999 |
| WO | WO 0100262 A1 | * | 1/2001 |
| WO | 0127348 A1 | | 4/2001 |
| WO | WO 0127348 A1 | * | 4/2001 |
| WO | 0141846 A | | 6/2001 |
| WO | 2009103336 A1 | | 8/2009 |

OTHER PUBLICATIONS

International Search Report and Written Opinion for PCT/EP2005/002131 mailed Jul. 22, 2005.

* cited by examiner

POWDER INHALER HAVING A NOZZLE WITH A PLURALITY OF CHANNELS

RELATED APPLICATIONS

This application claims the benefit under 35 USC 119(a) of German Patent Application No. 10 2004 012 093 filed Mar. 5, 2004, which is incorporated herein in its entirety.

BACKGROUND OF THE INVENTION

1. Field of the Invention

The invention relates to a powder inhaler with a mouthpiece for dispersing pharmaceutical medicament formulations, which has an auxiliary energy source in the form of a pressure medium system, and with a device for supplying a powder formulation, wherein on activation of the pressure medium system a gaseous pressure medium released by the pressure medium system forms an aerosol with the powder formulation such that the powder particles are present in dispersed form in the gaseous pressure medium.

Powder inhalers of this kind are needed for preparing inhalable medicaments. For diseases of the pulmonary and bronchial region, in particular, the medicaments are required and provided as inhalable pharmaceuticals (inhalants).

2. Description of the Prior Art

Within the scope of the present invention, the term "medicament" refers to the active ingredient of a pharmaceutical that is usually also known as a drug or active substance.

The term "medicament formulation" refers to powdered formulations that contain the medicament and are suitable for administration by inhalation in humans or animals. Usually, the active substance is mixed with adjuvants and additives.

In inhalers, the formulations are normally stored or kept in a reservoir and, for this reason, the formulations used must have sufficient stability on storage. Excipients may be added to the medicament for this purpose, to adjust the physicochemical properties which affect the quality-determining parameters, such as availability and durability in a desirable manner.

The medicament formulation stored in the powder inhaler is nebulized and breathed in by the patient as an aerosol. The medicament is prepared in an inhalable form.

However, in this process, it is not usual for the entire measured dose to be expelled as an aerosol, but only part of it. This is due to the fact that some of the powder formulation is left behind in the storage container, merely subjected to turbulence, and then re-deposited elsewhere in the inhaler.

The proportion of the measured dose that leaves the mouthpiece of the powder inhaler is referred to as the delivered dose. Powder particles can only enter the lungs during the inhaling process if the aerodynamic particle diameter is less than 5 µm. The result of this is that only a proportion of the delivered dose can actually reach the lungs. This proportion can only be determined by laborious tests on the patient. For this reason, in vitro tests have been developed in which a simple laboratory experiment is used to determine the aerodynamic fine content, which corresponds to the lung-bound part of the delivered dose. The aerodynamic fine content is defined as the proportion of the measured dose in percent that has an aerodynamic particle diameter of less than 5.8 µm.

Within the scope of the present invention, the aerodynamic particle diameter is the particle diameter that corresponds to the equivalent diameter of a ball of density 1 g/cm$^3$ that has the same sedimentation speed in air as the examined particle. To achieve the highest possible aerodynamic fine particle content, the following considerations are crucial.

First of all, a powder formulation must be prepared which contains the medicament in micronized form. The majority of all medicament particles should range from 1-5 µm in size. As micronized powders, being bulk materials, exhibit a high tendency to form particle agglomerates, the powder formulation usually contains excipients that make it easier to break up the micronized medicament particles and also increase their flow properties. Another parameter that is relevant to the quality of the powder formulation is its chemical and physical stability. Chemical stability is ensured if the medicament does not change into breakdown products on storage. Physical stability indicates that the aerodynamic fine content measured does not change during the storage period.

A suitable powder inhaler must convert a defined quantity of the powder formulation, i.e., the measured dose, into an aerosol during the inhaling process by the patient, while the highest possible values must be achieved for the delivered dose and the aerodynamic fine particle content. To achieve this, an important function of the powder inhaler is to break up the particle agglomerates of the medicament contained in the bulk powder formulation as efficiently as possible, as larger particles are deposited in the mouth and throat when breathed in and only particles with aerodynamic particle diameters of less than 5 µm reach the lungs. Thus, there is a more or less great difference between the proportion of the delivered dose based on the measured dose and the aerodynamic fine particle content, which is critically influenced by the efficiency of nebulization.

Against the background of the above remarks, the particle size must be reproducible within narrow limits so as to prevent fluctuations in the delivered dose and the aerodynamic fine content. On each actuation of the inhaler, roughly the same amount of medicament should be administered, while the delivered doses should have roughly the same size distributions of the particles of medicament.

However, from the point of view of efficiency and the most economical use of medicaments, it is also desirable to produce the largest possible aerodynamic fine particle content, as defined above.

In the prior art, there are basically two different systems of powder inhalers.

First, the so-called "passive" inhalers generally use the air breathed in by the patient to nebulize the powder formulation without any additional auxiliary energy sources—for example in the form of compressed air. These powder inhalers are designed so that powder is either contained in a prefabricated capsule in the form of a single dose (premetered dose), for example, or a number of premetered doses are held in readiness in a multi dose container inserted in the inhaler. During use, the capsule or one of the multi dose containers is pierced and the powder is emptied out and nebulized using the air breathed in by the patient.

The powder may also be present in the inhaler as a powder supply (bulk powder), an individual dose being prepared by means of a metering device before being transported out of the inhaler in the patient's air stream.

It is obvious that, with the powder inhalers described, the aerodynamic fine particle content is highly dependent on the patient's breathing maneuver.

Against the background of the above remarks it is now common to use so called "active" powder inhalers that use stored energy, e.g., pressurized gas. By using the pressurized gas for controlled expulsion and nebulization of the powder formulation, the process is made independent of the patient's breathing.

In order to achieve the break up of lumps and efficient nebulization and obtain the desired particle size and particle size distribution, essentially two methods have been used in the prior art.

In the case of some inhalers described in the literature, the breaking up of the powder is assisted by the impact of the particles on so called "impact surfaces." Easing pressure, for example, the powder particles are deliberately directed against these impact surfaces to break up the particles. However, the result of this is that some of the powder particles striking the impact surface remain stuck to it and are deposited thereon. As a result, it is not possible to achieve a highly accurate and reproducible dosage as the powder particles deposited can accidentally be released again during subsequent inhalations.

One disadvantage is that, when pressurized gases are used to break up the lumps in powder formulations, very high aerosol speeds are reached. Very high aerosol speeds in turn mean that the proportion of the dose that reaches the lungs is reduced. Therefore, for powder inhalers operating with pressurized gases, additional spacers/separators are provided that have the task of reducing the speed of the aerosol particles formed.

These spacers/separators (or break up chambers), in which the speed of the powder particles is decelerated, are arranged in front of the mouthpiece of the inhaler and make the inhaler bulky and awkward to use. Inhalers for the pharmaceutical field should, however, be small and convenient so that the patient can carry the inhaler about with them at all times.

SUMMARY OF THE INVENTION

Against this background, the aim of the present invention is to provide a powder inhaler for dispersing pharmaceutical powder formulations with which the problems of conventional powder inhalers known from the prior art are eliminated or, at the least, reduced, and with which, in particular, a high content of solid particles less than 5.8 µm in size is produced.

This objective is achieved by means of a powder inhaler of the generic type that is characterized in that, in the inhaler, there is provided a nozzle through which the aerosol flows before leaving the inhaler and in that the nozzle is a multi-channel nozzle, the channels of which are inclined to one another at such an angle that the aerosol jets flowing through them meet downstream behind the nozzle.

DESCRIPTION OF THE DRAWINGS

Hereinbelow, the invention will be described in more detail with reference to several embodiments shown in the two figures of drawings. In these drawings.

In the description that follows, identical parts have been given the same reference numerals.

DESCRIPTION OF THE INVENTION

Figure 1:
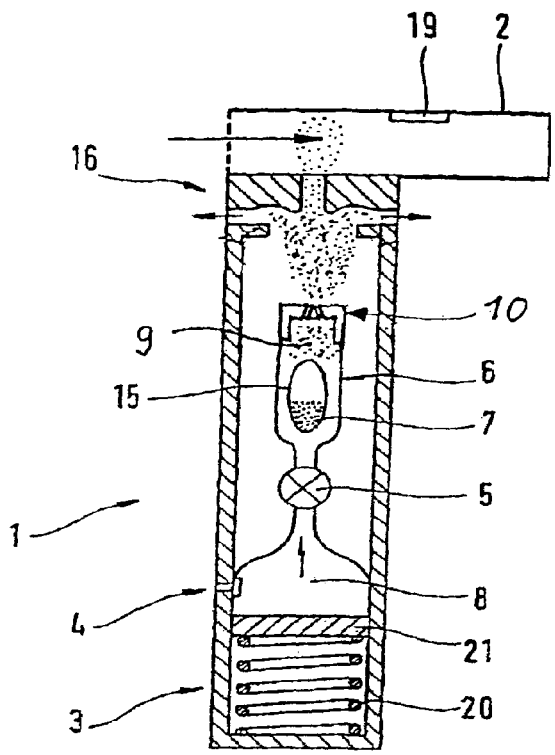
FIG. 1 is a diagrammatic view of a first embodiment of a powder inhaler, in side view, in section.

There is provided a powder inhaler of the generic type that is characterized in that, in the inhaler, there is provided a nozzle through which the aerosol flows before leaving the inhaler and in that the nozzle is a multi-channel nozzle the channels of which are inclined to one another at such an angle that the aerosol jets flowing through them meet downstream behind the nozzle.

In the powder inhaler according to the invention, the pressure medium carries the powder from the powder supply and transports it through at least two channels of the nozzle. Alternatively, it is also possible to use a powder inhaler in which a flow is generated by the patient's breathing in order to transport the powder from the powder supply and the channels of the nozzle.

The nozzle according to the invention is characterized in that powder particles with a high kinetic energy are produced, with the result that the fine particle content is correspondingly high. The particles are then decelerated again by the jet impact and the energy released is used to disperse the powder. A major advantage of this arrangement is that no surfaces of the device are involved in decelerating the aerosol and no or only very slight powder residues are left behind.

According to a particularly preferred embodiment, the nozzle is a two-channel nozzle the channels of which are inclined at an angle $\alpha$ to one another, where $0° < \alpha \leq 180°$. The most suitable angle is determined as a function of, among other things, the composition of the powder formulation and other parameters.

According to an advantageous feature, the powder formulation mixed with the pressure medium is supplied simultaneously to all the channels of the nozzle. In this way a totally homogeneous aerosol is formed downstream of the nozzle.

According to another feature, the pressure medium is supplied to at least one channel and a mixture of powder formulation and pressure medium is supplied to the other channels. As a result, at least one jet stream from the pressure medium strikes at least one jet stream containing the pre-dispersed powder.

Admittedly, the kinetic energy of the powder particles is substantially reduced by the jet impact, but the remarks that follow refer to the further behavior of the aerosol downstream of the nozzle.

As an excessively high flow speed reduces the fine particle content which is capable of reaching the patient's lungs during the inhalation process, the speed at the exit from the mouthpiece should be not more than 20 m/s, preferably not more than 10 m/s, more particularly not more than 5 m/s.

As high flow speeds have to be produced for breaking up the powder as it passes through the nozzle, it is generally necessary to reduce the aerosol speed along the path between the nozzle and mouthpiece. This can be achieved in various ways, so that there is no need to use the powder inhaler according to the invention together with a spacer. Specifically, the following results are preferably obtained:

The aerosol leaving the nozzle outlets can be mixed in various ways with the patient's breathed-in air as it travels between the nozzle and mouthpiece.

The production of a turbulent flow of the patient's breathed-in air is a suitable measure for this purpose. The aerosol cloud passing through the nozzle channels is injected into the turbulence of the breathed-in air, thereby reducing the forward component of the speed of the aerosol cloud.

Designing the nozzle so that the breathed-in air and the aerosol flows emerging from the nozzle channels are directed against each other, again resulting in deceleration, is another measure for reducing the flow rate of the aerosol cloud.

In an alternative embodiment the entry opening for the breathed-in air is located askew or perpendicular to the direction of flow of the nozzle.

In order to reduce the speed of the aerosol cloud leaving the nozzle channels in the inhaler, it may prove advantageous to mix this aerosol cloud with an air current in counter current thereto. It is advantageous if this contrary air current is produced by the breathing-in process of the user. Usually, in a powder inhaler, provision is made for the patient to breathe in air when breathing in the cloud of powder in order to ensure an inspiration process free from complications. For this purpose, air slots may be formed in the mouthpiece, for example, through which the patient automatically breathes in air at the same time as the cloud of particles. Within the scope of the powder inhaler according to the invention, these air inlet openings may be formed so that the in-flowing air meets the aerosol cloud either as a simple counter current or as an air current striking the aerosol cloud, thereby reducing its speed. This objective can be achieved in terms of construction by having the mouthpiece located perpendicular to the path traveled by the aerosol cloud as it leaves the nozzle openings. The air inlet slots are then also perpendicular to the mouthpiece and are formed in a line with the exit path of the aerosol cloud from the nozzle, but precisely opposite the nozzle. Expressed in simple terms this construction would be in the form of a T-shaped member, with the nozzle for the aerosol cloud and the air inlets for the counter current of air determining the end points of the crosspiece of the T while the mouthpiece corresponds to the base of the T.

In an alternative embodiment, the nozzle channels and the air inlet holes open into a turbulence chamber, are spun around with one another therein, and then leave through a mouthpiece.

A turbulence chamber of this kind may, in the simplest case, be a hollow chamber into which the nozzle opens at one point. The air inlet can then open into the chamber precisely opposite the nozzle or preferably perpendicular thereto or at least offset at an angle. The chamber then has an exit to the mouthpiece.

In the simplest case, the powder inhaler according to the invention consists of a housing with a mouthpiece. In front of the mouthpiece and inside the housing is the nozzle described above. Also, on the inside is a chamber for accommodating the powder formulation that is to be nebulized.

Preferably, the powder inhaler comprises a pressure system that directs a pressurized gas on to the quantity of powder formulation to be dispersed so that the latter is dispersed and the resulting aerosol is conveyed through the nozzle system described above into the mouthpiece, while coarser particles are broken up. The powder inhaler has channels inside it which define the path of the pressurized gas released through the inhaler into the mouthpiece. In the chamber for accommodating the powder formulation intended for dispersion, the powder may be loose or may be in a container, e.g., in a capsule or blister that is opened before the pressurized gas passes through, such that the pressurized gas is able to carry the powder along leaving substantially no residues. In the case of a single-use inhaler, this device does not have any other supply for further doses of the powder formulations. In the case of a device intended for repeated use, the inhaler may have one or more reservoirs for the powder formulation. Thus, the reservoir may simply be a chamber containing the powder mixture in loose form and, from there, measured quantities are carried into the nebulizing chamber. Alternatively, the reservoir may be a collection of capsules that are filled with the powder formulation and introduced mechanically or manually into the nebulizing chamber. Finally, the reservoir may also be a blister with a plurality of pouches for the powder formulation, in which cases one of these pouches is introduced into the nebulizing chamber. Reservoir systems of this kind, and the transfer of the powder formulation from the reservoir into the nebulising chamber, are known from the prior art and will therefore not be discussed in detail at this point.

Regarding the pressure medium system, the powder inhaler according to the invention may have a cartridge of compressed air, a cartridge filled with a gas other than air, e.g., nitrogen, carbon dioxide, a noble gas, such as helium or argon, or even a fluorohydrocarbon, an alkane, and the like. In advantageous embodiments of the powder inhaler, the pressure medium system is a system that takes in air from the environment and then releases the air in controlled manner under compression and under pressure in the direction of the formulation that is to be nebulized. On the one hand, air is the most acceptable medium for the patient as a carrier for the powder particles. On the other hand, it is freely available. The preferred embodiment of the powder inhaler takes the required amount of air from the atmosphere, compresses it, and then uses it as a carrier medium for the powder formulation. There is no need to change the pressure medium system, as would be the case with a pressure medium stored in a cartridge.

However, in other advantageous embodiments of the powder inhaler, the pressure medium system comprises a cartridge that supplies a pressure medium under pressure. In contrast to the powder inhaler described previously, this embodiment is less complex in structure and therefore cheaper and smaller in size.

In any case, the pressure medium system is such that the user of the inhaler can achieve a controlled delivery of pressure medium.

There are advantageous embodiments of the powder inhaler that are characterized in that the device for supplying the powder formulation is arranged between the pressure medium system and the nozzle, such that the pressure medium has to go past the device, while preferably the device for supplying the powder formulation comprises a powder-filled capsule. Preferred embodiments of the powder inhaler are those wherein the capsule is replaceable as the consumable material. A mechanism is provided on the powder inhaler by means of which the capsule can be replaced.

In this embodiment, the pressure medium flows through the device for supplying the powder formulation and distributes or picks up the powder, so that after flowing through the supply chamber the desired primary aerosol is formed.

Alternatively, it is possible to have an embodiment without a pressure medium. In this case, the flow is generated by the air stream of the patient produced on breathing in, so as to form the desired primary aerosol.

In advantageous embodiments of the powder inhaler, the device for supplying the powder formulation comprises a multi dose blister container. Multi dose blister containers of this kind may be linear, such as a blister strip, flat, such as a blister disk or blister rings, or three-dimensional, such as cylindrical or polygonal bodies. Multi dose systems of this kind may contain 2 to 90 doses, preferably 5 to 60 doses, more particularly 7 to 30 doses, each dose being stored in a separate pocket or pouch which is opened by suitable means on use.

As already stated, powder inhalers in which air is provided as the pressure medium are preferred.

If the pressure medium system is not manually operated by its nature, but comprises a control means, e.g., in the form of an actuator valve that has to be operated and that releases the pressure medium by opening or closing, it is advantageous to have embodiments of the powder inhaler that provide a through-flow sensor in the mouthpiece to measure the flow of the breath of the patient and, on reaching a certain, predetermined breath flow speed, to generate an input signal for the pressure medium system or its control member.

The through-flow sensor measures the speed of the air current as the patient breathes in and generates an input signal which acts upon the control member. The control member opens in response to the input signal and thereby allows the pressure medium to flow out when the through-flow rate is in a range suitable for inhalation, but the control member does not release the pressure medium system when the through-flow rate is outside the preferred range. This automatic opening and closing does away with the need to provide an additional actuating device and makes the inhaler more user friendly and easier to handle.

The powder inhaler according to the invention has the following advantage over the prior art:
- an aerosol is produced from bulk powder that is pre-dosed in a suitable container, while the energy available in the form of a pressurized gas is used to overcome the forces of agglomeration of the micronized powder particles with one another so as to produce an aerosol with a comparatively above-average content of solid particles less than 5.8 μm in size;
- the system described here does not need fluorinated propellant gases or fluorochlorohydrocarbons;
- the production of the aerosol and the particle size distribution achieved are independent of the patient's breathing maneuver;
- the powder residues in the device are kept to a minimum by the construction, as the breaking up of the clumps of powder is achieved by the impacting of a number of jet streams (jet impaction) and not by impacting on impact surfaces;
- the inhaler described is small and can easily be carried around by the patient;
- there is no need to use the device with a "spacer," as in other "active" powder systems (see WO 99/6249), as a slowly moving aerosol cloud is produced in the device by suitable measures.

FIG. 1 is a diagrammatic representation of a first embodiment of a powder inhaler 1 for dispersing pharmaceutical medicament formulations, in side view and in section.

The powder inhaler 1 has at its top end a mouthpiece 2. It has an auxiliary energy source in the form of a pressure medium system 3, the pressure medium system 3 being equipped with a pump (20, 21) that is connected to the atmosphere through a valve 4 and uses the ambient air as a pressure medium, which is generally indicated as reference numeral 8.

Ambient air is brought into the powder inhaler 1 through a valve 4 by the downward movement or expansion of a piston 21, which acts against a spring 20. The ambient air becomes the pressure medium 8 by compression by the upward movement of the piston, which is acted upon by the spring 20. There is no need to replace the pressure medium system, as would be the case when using a pressure medium stored in a cartridge.

The pressure medium 8 leaves the pressure medium system 3 through a control member or actuator valve 5. In the embodiment shown in FIG. 1, a through-flow sensor 19 is provided in the mouthpiece 2. The through-flow sensor 19 measures the air current as the patient breathes in—the through-flow rate—and generates an input signal that acts upon the actuator valve 5. The actuator valve 5 is allowed to open and the pressure medium 8 is allowed to flow out of pressure medium system 3 when the through-flow rate is in a range suitable for inhalation, while the actuator valve 5 is prevented from opening if the through-flow rate is outside this preferred range. This automatic control of the actuator valve 5 makes the device more user-friendly and achieves optimum conditions during inhalation.

After leaving the pressure medium system 3, the pressure medium 8 flows through a device for supplying 6 the powder formulation 7. The device for supplying 6 the powder formulation 7 comprises a capsule 15 filled or loaded with powder formulation 7.

In this embodiment the pressure medium 8 flows through the device for supplying 6 the powder formulation 7 and picks up some of the powder formulation 7, so that, after flowing through the supply chamber, the desired primary aerosol 9 is obtained that comprises particles of the powder formulation 7 dispersed in the pressure medium 8.

FIG. 2a now diagrammatically shows the multi-channel nozzle 10 in the form of a two-channel nozzle with two channels 11 and 12. The channels 11 and 12 are inclined to one another at an angle α. The angle α may be between 0° and 180°. The inclination causes an aerosol jet leaving the channel 11 to impact with an aerosol jet leaving the channel 12 and break up the powder particles. In the embodiment shown in FIG. 2a, the two channels 11 and 12 are uniformly charged with a powder/gas mixture.

Figure 2:
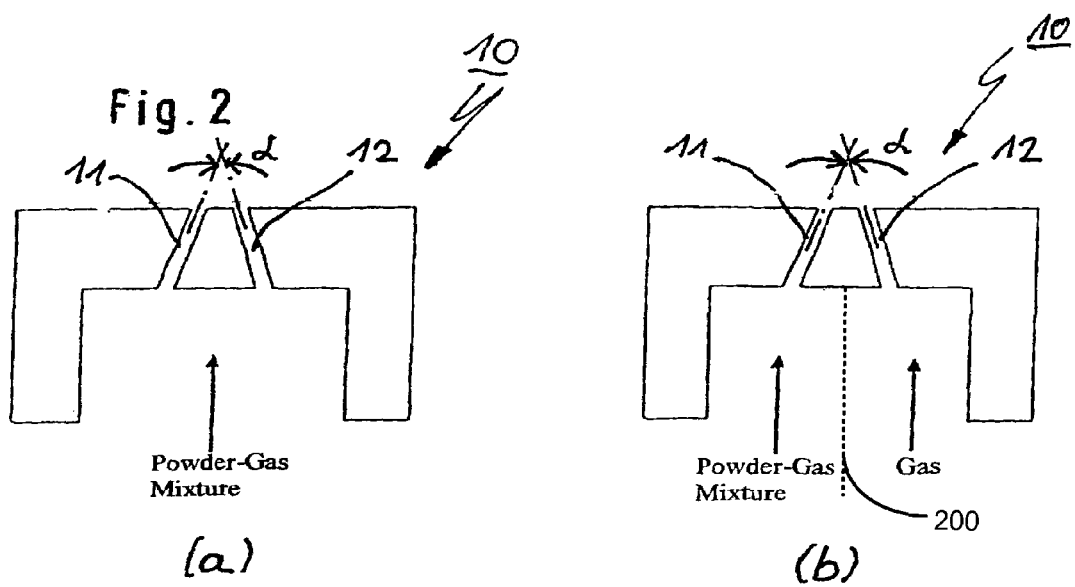
FIG. 2a is a diagrammatic representation of the multichannel nozzle of a powder inhaler in side view, in section.
FIG. 2b shows the nozzle according to FIG. 2a in another type of operation.

FIG. 2b shows the nozzle 10 according to FIG. 2 in a different mode of operation. Here, pressure medium 8 is supplied to a channel 12 as pure gas, whereas a powder/gas mixture is supplied to the channel 11. The element 200 shows a schematic partition between the pressure medium 8 and the powder/gas mixture wherein only the pressure medium is supplied to the channel 12.

As already stated, the aerosol jets may strike one another at any desired angle from 0° to 180°, at any desired distance from the surface of the nozzle 10, and at any desired speed. The ratio of the parameters determines the degree of dispersion and the speed of the secondary aerosol 13 produced from the primary aerosol 9 by the nozzle 10.

Figure 3:
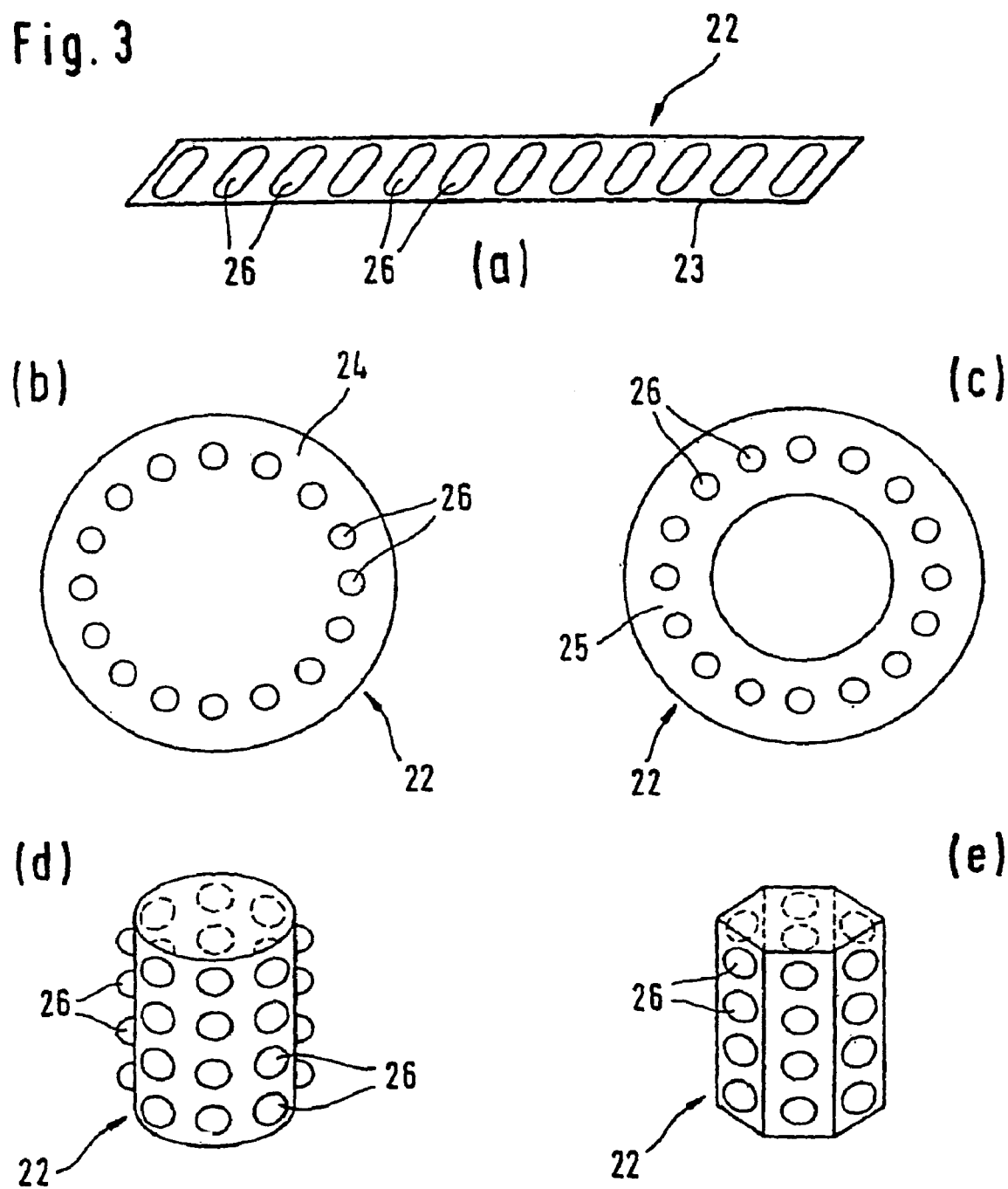
FIG. 3a is a diagrammatic representation of a first embodiment of a multi dose blister container for supplying the powder formulation, in side view.
FIG. 3b is a diagrammatic representation of a second embodiment of a multi dose blister container for supplying the powder formulation, in side view.
FIG. 3c is a diagrammatic representation of a third embodiment of a multi dose blister container for supplying the powder formulation, in side view.
FIG. 3d is a diagrammatic representation of a fourth embodiment of a multi dose blister container for supplying the powder formulation, in perspective view.
FIG. 3e is a diagrammatic representation in perspective view of a fifth embodiment of a multi dose blister container for supplying the powder formulation.

FIG. 3a shows a diagrammatic representation, in side view, of a first embodiment of a multi dose blister container 22 for supplying the powder formulation. The multi dose blister container 22 is of linear construction in the form of a blister strip 23 and comprises a number of capsules 26 arranged in a row, each capsule 26 containing a single dose. The capsule 26 in use is opened by suitable means.

FIG. 3b shows a diagrammatic representation, in side view, of a second embodiment of a multi dose blister container 22 for supplying the powder formulation. The multi dose blister container 22 is of flat construction in the form of a blister disk 24 and comprises a plurality of capsules 26 arranged in a circle.

FIG. 3c is a diagrammatic view—a side view—of a third embodiment of a multi dose blister container 22 for supplying the powder formulation. The multi dose blister container 22 is constructed flat as a blister ring 25 and comprises a plurality of capsules 26 arranged in a circle.

FIG. 3d shows a diagrammatic representation, in side view, of a fourth embodiment of a multi dose blister container 22 for supplying the powder formulation, in perspective view. The multi dose blister container 22 is of three-dimensional construction in the form of a cylindrical body. Multi dose systems of this kind may contain 2 to 90 doses, preferably 5 to 60 doses, in particular 7 to 30 doses, each dose being stored in a separate capsule 26 which is opened by suitable means on use.

FIG. 3e shows a diagrammatic representation, in perspective view, of a fifth embodiment of a multi dose blister container 22 for supplying the powder formulation. The multi dose blister container 22 is of three-dimensional construction, as in FIG. 3d, in the form of a polygonal body.

Figure 4:
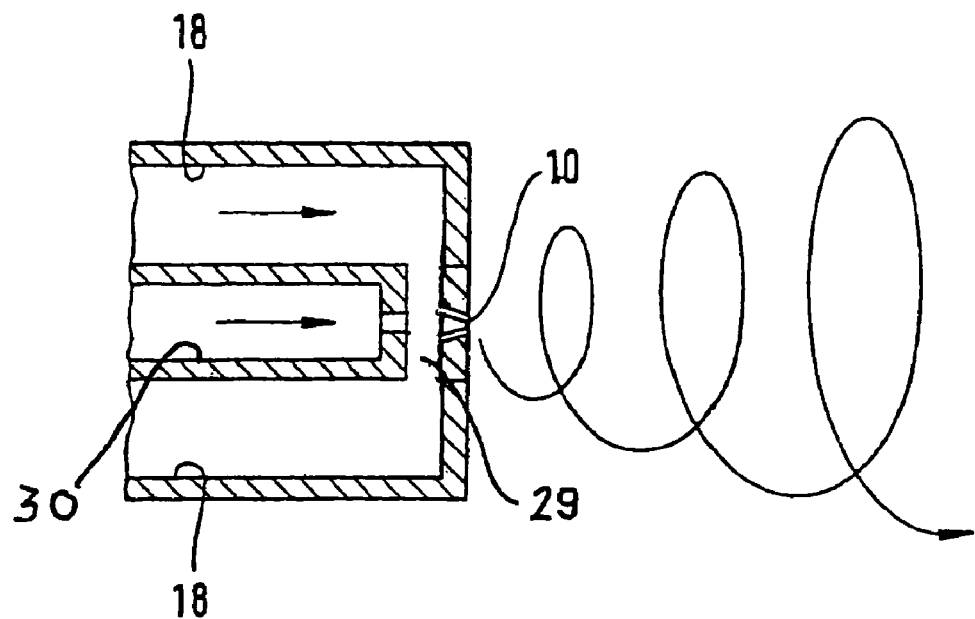
FIG. 4 is a diagrammatic representation, in side view and in section, of a first embodiment of a device for delaying the aerosol flow.
Figure 5:
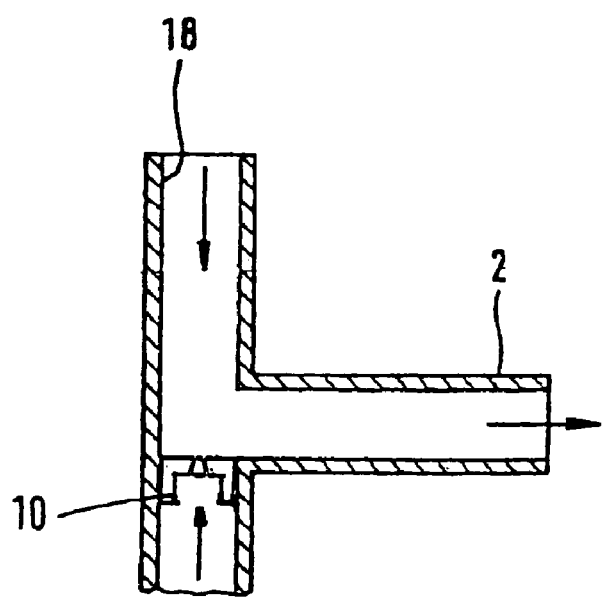
FIG. 5 is a diagrammatic view of a second embodiment of a device for delaying the aerosol flow in side view and in section.

FIG. 4 shows a diagrammatic representation, in side view and in section, of a first embodiment of a device for delaying the flow of aerosol. The two flows, both the flow of inspired air in the inlet channel 18 and the primary aerosol flow in the channel 30, initially run parallel in two coaxial tubes, the inspired air being transformed in the turbulence chamber 29 into a turbulent flow. Jets of the primary aerosol flow are injected into the turbulence chamber by the nozzle to mix with the inspired air. The secondary aerosol in this turbulent flow has a lower flow velocity compared to the jets of the primary aerosol from the nozzle.

FIG. 5 shows a diagrammatic representation, in side view and in section, of a second embodiment of a device for delaying the aerosol flow. The flow of inspired air and the secondary aerosol flow are directed towards one another. As they come into contact and the flow is deflected the forward speed of the aerosol flow is reduced.

We claim:

1. A powder inhaler comprising:

a device operating to supply a powder formulation, a pressure medium system operating to release a pressure medium, the pressure medium operating to form a primary aerosol with the powder formulation, a nozzle comprising a plurality of channels wherein only the pressure medium flows through at least one channel of the nozzle and the primary aerosol flows in remaining channels of the nozzle such that jets of the primary aerosol and the pressure medium are produced, the channels being arranged such that the jets of the primary aerosol and the pressure medium are directed towards one another, whereby the jets of the primary aerosol and the pressure medium at least partially impact with one another to form a secondary aerosol, and a mouthpiece in communication with the nozzle such that the secondary aerosol flows from the nozzle towards the mouthpiece, wherein the jets of the primary aerosol and the pressure medium separately have a primary flow speed, and wherein the secondary aerosol has a secondary flow speed that is lower than the flow speed of the jets of the primary aerosol, and the secondary aerosol flows towards the mouthpiece at the secondary flow speed.

2. The powder inhaler according to claim 1, wherein the nozzle comprises two channels that are inclined towards one another at an angle α, wherein $0° < \alpha \leqq 180°$.

3. The powder inhaler according to claim 1, wherein the primary aerosol is supplied to all the channels.

4. The powder inhaler according to claim 1, wherein the pressure medium system comprises a pump operating to convert atmospheric air into the pressure medium.

5. The powder inhaler according to claim 1, wherein the pressure medium system comprises a cartridge that supplies a pressure medium.

6. The powder inhaler according to claim 5, wherein air is provided as the pressure medium.

7. The powder inhaler according to claim 5, wherein $N_2$, $CO_2$, argon, or helium is provided as the pressure medium.

8. The powder inhaler according to claim 1, wherein the device for supplying the powder formulation is arranged between the pressure medium system and nozzle.

9. The powder inhaler according to claim 1, wherein the device for supplying the powder formulation comprises a capsule filled with powder.

10. The powder inhaler according to claim 9, wherein the capsule is replaceable as a consumable material.

11. The powder inhaler according to claim 1, further comprising a through-flow sensor that sends an input signal to the pressure medium system when the through-flow sensor detects a pre-defined through-flow.

12. The powder inhaler according to claim 11, wherein the pressure medium system comprises an actuator valve that controls the release of the pressure medium, and wherein the actuator valve opens in response to the input signal.

13. The powder inhaler according to claim 1, further comprising a mouthpiece, wherein a turbulent flow is produced between the nozzle and the mouthpiece by inspired air from an inlet channel.

14. The powder inhaler according to claim 1, wherein the nozzle and an inlet channel for inspired air are arranged so that the secondary aerosol and the inspired air are directed towards one another.

15. The powder inhaler according to claim 1, wherein the nozzle and an inlet channel for inspired air are arranged so that the secondary aerosol and the inspired air strike one another at an angle.

16. The powder inhaler according to claim 1, wherein the secondary aerosol and inspired air from an inlet channel are mixed in a turbulence chamber.

17. The powder inhaler according to claim 1, wherein the secondary flow speed is not more than 20 m/s.

18. The powder inhaler according to claim 1, wherein no surfaces are involved in decelerating the primary aerosol to create the secondary aerosol.

19. The powder inhaler according to claim 1, wherein the mouthpiece includes at least one air inlet for a current of air such that the current of air mixes with, and further decelerates, the secondary aerosol.

20. The powder inhaler according to claim 19, further comprising a T-shaped member such that the nozzle for the aerosol and the at least one air inlet are positioned to correspond to one or more end points of a crosspiece of the T-shaped member while the mouthpiece is positioned to correspond to a base of the T-shaped member.

21. The powder inhaler according to claim 1, wherein the mouthpiece is located perpendicular to the flow path.

22. The powder inhaler according to claim 1, further comprising a valve connected to the pressure medium, wherein the valve operates to permit ambient air to enter the pressure medium system such that the ambient air is used at least partially as the pressure medium.

23. The powder inhaler according to claim 1, further comprising a turbulence chamber in communication with at least one inlet channel such that any inspired air that enters the device from the at least one inlet channel is transformed in the turbulence chamber into a turbulent flow, wherein the at least one inlet channel runs parallel to a channel through which the primary aerosol travels for a predetermined distance, and the at least one inlet channel runs transverse to the turbulence chamber between an opening of the channel through which the primary aerosol travels and the nozzle such that the turbulent flow mixes with the primary aerosol.

* * * * *